(12) United States Patent
Takahashi

(10) Patent No.: US 8,194,954 B2
(45) Date of Patent: Jun. 5, 2012

(54) MEDICAL REPORT SYSTEM, AND MEDICAL REPORT MAKING APPARATUS AND METHOD

(75) Inventor: Noriyuki Takahashi, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 930 days.

(21) Appl. No.: 12/212,721

(22) Filed: Sep. 18, 2008

(65) Prior Publication Data
US 2009/0087048 A1 Apr. 2, 2009

(30) Foreign Application Priority Data
Sep. 27, 2007 (JP) .................................. 2007-252595

(51) Int. Cl.
*G06K 9/00* (2006.01)
(52) U.S. Cl. .......................... 382/128; 382/159; 382/305
(58) Field of Classification Search .................. 382/128, 382/159, 305
See application file for complete search history.

(56) References Cited

U.S. PATENT DOCUMENTS
2004/0081342 A1* 4/2004 Sato .............................. 382/128

FOREIGN PATENT DOCUMENTS
JP 2004-305289 A 11/2004

* cited by examiner

*Primary Examiner* — Theresa T Doan
(74) *Attorney, Agent, or Firm* — Sughrue Mion, PLLC

(57) ABSTRACT

On a report making screen, medical images taken from a patient are displayed in a viewer. When an area of concern, such as an abnormal shadow, is designated in any of the displayed medical images, the medical images containing the area of concern are chosen. By drag-and-dropping one of the chosen images to an assigned position in a comment editing zone of the report making screen, a three-dimensional image reconstituted of the chosen images is displayed as a confirmation image, wherein the designated area of concern is displayed distinguishably from other portion, enabling checking whether the choice of the images or the designation of the area of concern is correct or not. When the choice and designation is fixed, group data registering the chosen images as a group and position data relating to positions of the area of concern in the chosen images are memorized in linkage with the assigned position.

14 Claims, 10 Drawing Sheets

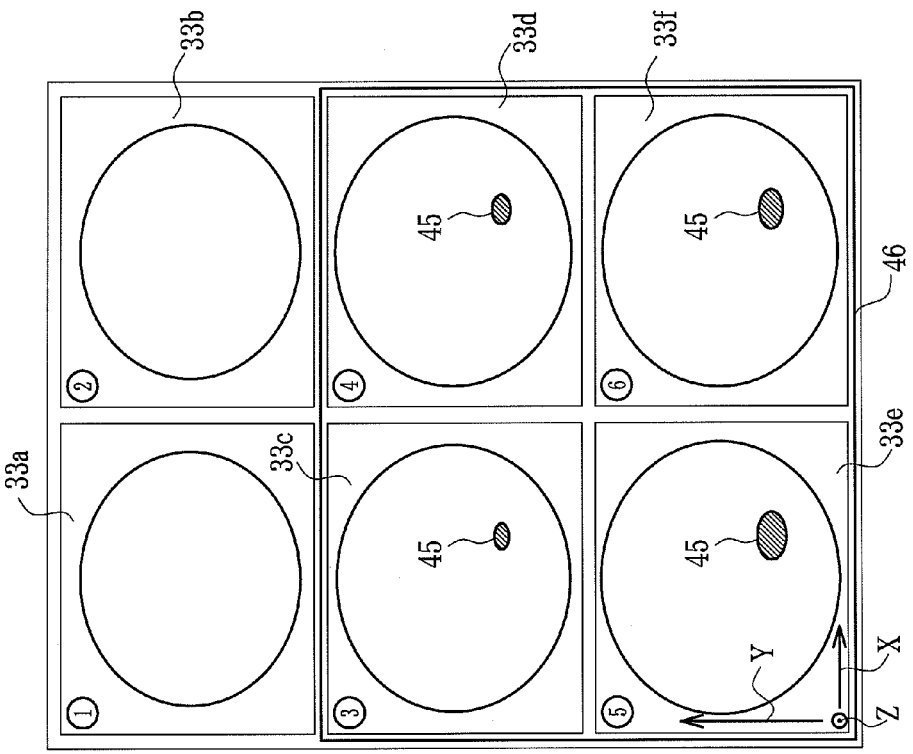
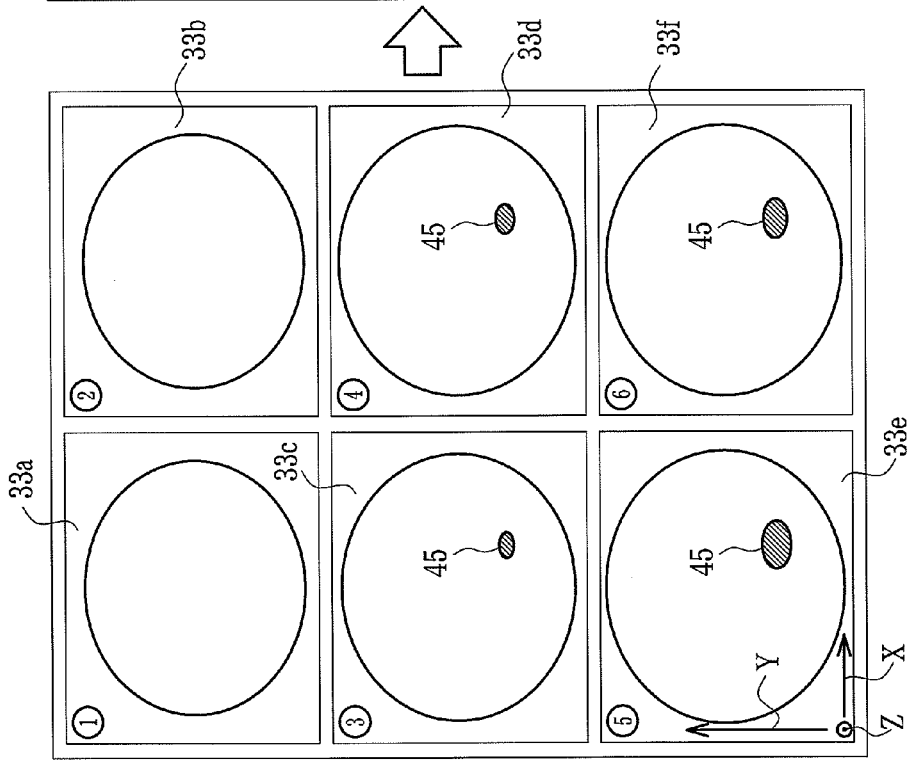

MEDICAL REPORT SYSTEM, AND MEDICAL REPORT MAKING APPARATUS AND METHOD

FIELD OF THE INVENTION

The present invention relates to a medical report system for making a medical report about medical images and displaying the medical report. The present invention relates also to a medical report making apparatus and a medical report making method for this medial report system.

BACKGROUND OF THE INVENTION

In medical facilities like hospitals, a variety of medical examination apparatuses, such as modalities for CR (computed radiography), CT (computer tomography), MRI (magnetic resonation imaging), PET (positron emission tomography) and ultrasonic diagnosis, have been widely used. Medical images taken from patients by the modalities are used in medical diagnoses, taking an important roll on determining the nature of a disorder of each individual patient.

For the diagnosis based on medical images, doctors of various diagnosis and treatment departments generally ask specialists of an image-interpretation department for an interpretation of the medical images. In the image-interpretation department, the doctor interprets the medical images and reports the interpretation. Then, the doctor in the diagnosis and treatment department examines the report on the image interpretation, hereinafter referred to as the medical report, to diagnose a disorder (an injury or a disease) of the patient.

Recently, in order to improve work efficiency in the medical field, computerization of medical images and charts has been promoted, and systems for making the above-mentioned image interpretation online have been suggested. For example, in a medical report making system disclosed in JPA2004-305289, such information that identifies a medical image and a corresponding location in the medical image is added to a comment in the medical report, so as to make it easy to recognize which location in the medical image the comment is referring to.

Since a target area of the above-mentioned medical inspection, such as an organ or a diseased site, extends three-dimensionally, it is general in the inspection like CT scanning or MRI scanning, e.g. tomography, to capture a series of medical images slicing across a body axis of a patient. Among these successive tomograms, one showing an area of concern is designed to be examined for diagnosis.

However, according to the above-mentioned prior art, if the area of concern is shown in many images, it is necessary to choose the images containing the area of concern each individually and then designate the area of concern in each of the chosen images to link it to a comment in the report. These procedures involve a possibility of making a mistake in choosing the images or designating the area of concern. Because this prior art does not consider checking or confirming the chosen image and the designated area of concern, there is a possibility of producing a medical report on the basis of the mistaken image or area of concern. Accuracy of the diagnoses will be worsened if they are made based on such inaccurate medical reports.

SUMMARY OF THE INVENTION

In view of the foregoing, a primary object of the present invention is to provide a medical report system for making and displaying a medical report, which makes it sure to choose exactly those medical images containing an area of concern or an affected site and designate those locations in the chosen medical images which show the area of concern, by making it easy to notice a mistake in the choice of the image or in the designation of the area.

Also, the present invention is objected to provide a medical report making apparatus and a medical report making method for this medial report system.

A medical report system of the present invention comprises an image display device for displaying a number of medical images taken from a test body; an image choosing device for choosing some medical images from among the displayed medical images; and an image display control device for processing data of the chosen medical images to produce and display a confirmation image on the image display device or another image display device, wherein the confirmation image represents an imaged site of the test body contained in the chosen images and is configured in a coordinate system with respect to a body axis of the test body.

Preferably, the medical report system further comprises an area designating device for designating an area of concern in the medical images, wherein the image choosing device chooses those medical images which contain the area of concern as designated by the area designating device, and the image display control device distinguishes the designated area and displays the designated area in a different manner from other portion in the confirmation image.

According to an embodiment, the medical images are tomograms taken from the test body along parallel slicing planes, and the image display control device reconstitutes from the chosen images a three-dimensional image of the imaged site as the confirmation image, wherein the chosen images are stacked up sequentially from the lower plane to the upper plane and are spaced from one another in an Z-axis direction of the coordinate system that is perpendicular to the slicing planes, at a constant interval defined based on a slice thickness used for tomography, and respective pixels of one chosen image are aligned with those pixels of another chosen image which correspond in XY coordinative position in the coordinate system.

According to another embodiment, the medical images are tomograms taken from the test body along parallel slicing planes, and the image display control device produces a density-added image from the chosen images by adding density values of respective pixels of one chosen image to density values of those pixels of another chosen image which correspond in position in XY directions of the coordinate system, which are parallel to the slicing planes, and displays the density-added image as the confirmation image.

Preferably, the medical report system further comprises a device for displaying and editing a report making screen that has a comment editing zone for inputting and editing comments on the medical images; a grouping device for producing group data that registers the chosen images as one group each time the choice of these medical images is fixed; and a linking device for storing the group data and position data relating to respective positions of the area of concern in the chosen images while making a linkage of the group data and the position data to an assigned position in the input comments.

A medical report making apparatus of the present invention comprises an image display device for displaying a number of medical images taken from a test body; a device for displaying and editing a report making screen that has a comment editing zone for inputting and editing comments on the medical images; an image choosing device for choosing some medical images from among the displayed medical images;

and an image display control device for processing data of the chosen medical images to produce and display a confirmation image on the image display device or another image display device, wherein the confirmation image represents an imaged site of the test body contained in the chosen images and is configured in a coordinate system with respect to a body axis of the test body.

A medical report making method of the present invention comprising steps of:

displaying a number of medical images taken from a test body;

inputting and editing comments on the medical images in a predetermined zone on a displayed screen;

choosing some medical images from among the displayed medical images;

processing data of the chosen medical images to produce a confirmation image, the confirmation image representing an imaged site of the test body contained in the chosen images in a coordinate system defined with respect to a body axis of the test body; and displaying the confirmation image.

Since the confirmation image produced from the chosen medical images is displayed, it is possible to check visually whether the choice of the images or the designation of the area of concern is correct or not. According to a preferred embodiment, an area of concern is designated in any of the displayed medical images, and the medical images containing the designated area of concern are chosen, and the designated area of concern is displayed distinguishably from other portion in the confirmation image. Thus, it becomes easy to notice a mistake in the choice of the image or in the designation of the area of concern, which ensures choosing exactly those medical images which contain the area of concern or designating those locations in the displayed medical images which show the area of concern.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein:

FIGS. 5A and 5B are explanatory diagrams illustrating a process of choosing and designating an area of concern;

DESCRIPTION OF THE PREFERRED EMBODIMENTS

Figure 1:
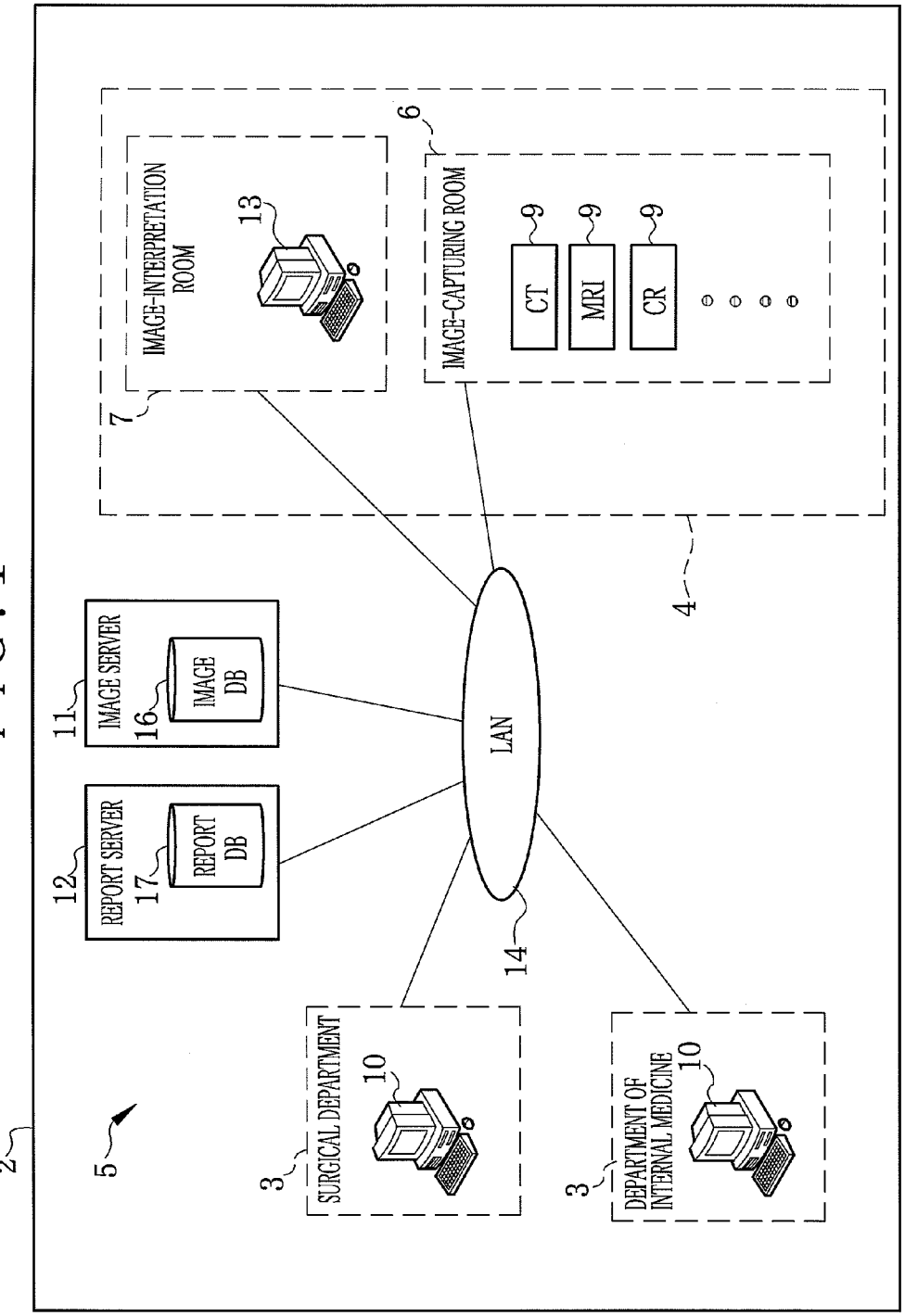
FIG. 1 is an explanatory diagram schematically illustrating a medical report system.

FIG. 1 illustrates a structure of a medical network system 5 that is a medical report system installed in a large-scale medical facility like a hospital 2. The hospital 2 is provided with various diagnosis-and-treatment departments 3, including a surgical department and a department of internal medicine, and an inspection department 4 for making medical inspections. The medical network system 5 is used for making reports on the medical inspections and referring to the reports. The inspection department is provided with image-capturing rooms 6 for capturing images from patients under examination, and an image-interpretation room 7 for interpreting the examination images taken in the image-capturing room 6. In the image-capturing rooms 6 are installed modalities 9, which are high-precision medical inspection apparatuses such as a CT scanner, a MRI scanner and a CR machine.

The medical network system 5 consists of diagnosis-and-treatment department terminals 10, an image server 11, a report server 12, a report making terminal (medical report making apparatus) 13 and a LAN (local area network) 14 interconnecting these components for communication.

The image server 11 is provided with an image database (DB) 16, whereas the report server 12 is provided with a report database 17. These databases 16 and 17 may be hard disc drives or the like. When a request for examination is sent to the inspection department 4, an inspection ID is given to each medical image as taken by the modalities 9, and is sent to the image server 11 via the LAN 14, to be stored in the image database 16. The report database 17 stores report data produced in the medical report making terminal 13, as will be described later. The diagnosis-and-treatment department terminals 10 are installed in the respective diagnosis-and-treatment departments 3, so that a doctor can apply for an examination or display the medical reports on the terminal 13.

Figure 2:
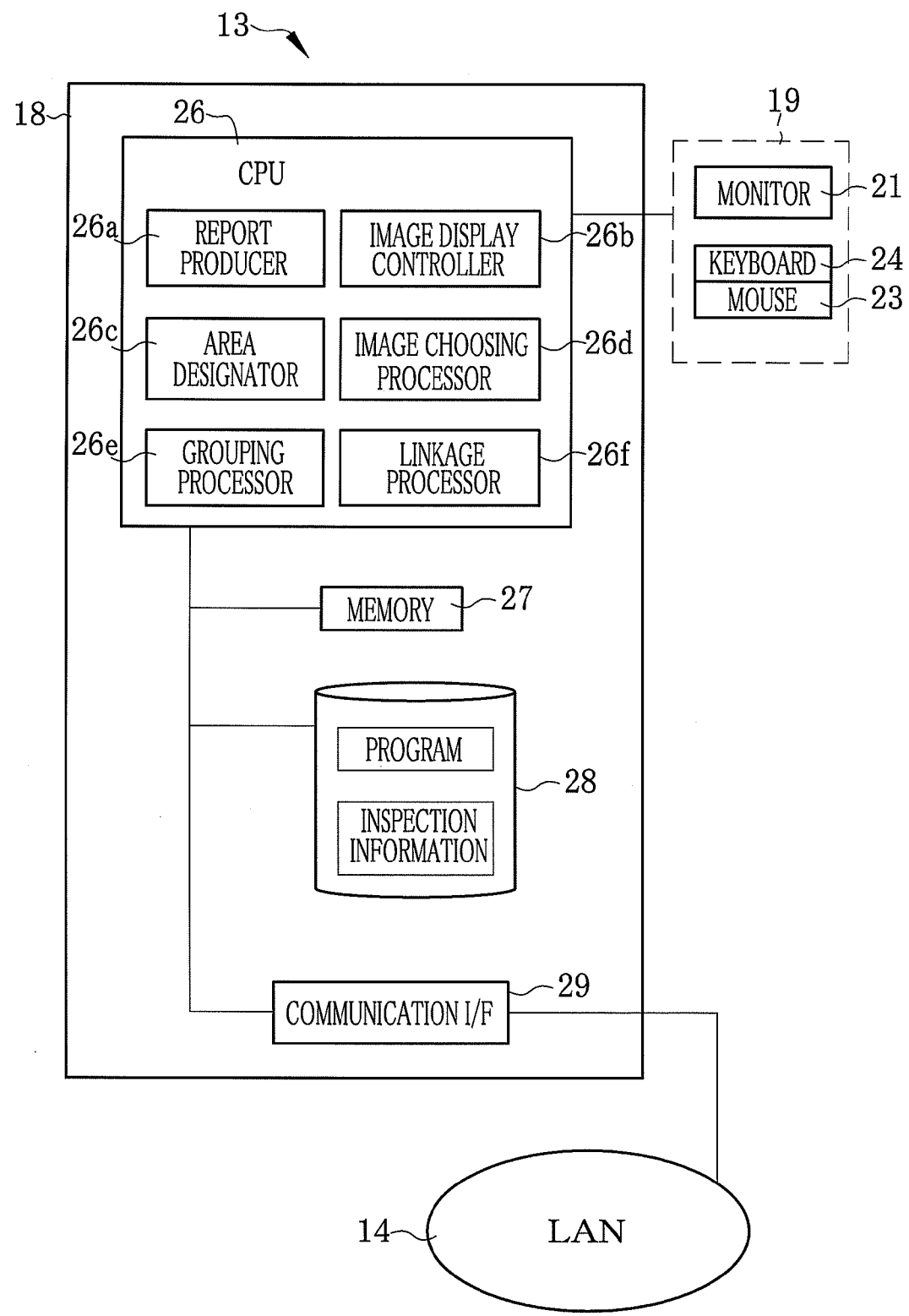
FIG. 2 is a block diagram schematically illustrating a structure of a medical report making apparatus.

The medical report making terminal 13 is installed in the image-interpretation room 7 of the inspection department 4, and is available for a doctor to make a medical report. For example, the medical report making terminal 13 is constituted of a personal computer or a workstation that is installed with a medical report making program. Specifically, as shown in FIG. 2, the medical report making terminal 13 consists of a main body 18 and a console 19. The console 19 is provided with a monitor 21, and input devices like a mouse 23 and a keyboard 24. The medical report making terminal 13 is also installed with a browser so that data as delivered to the browser is interpreted to constitute a report making screen 30 and output it to the monitor 21.

The main body 18 consists of a CPU (central processing unit) 26, a memory 27, a HDD (hard disc drive) 28 and a communication interface (I/F) 29. The HDD 28 is a well-known data storage device, storing an operating system, various programs, and inspection information which are linked with the medical images. The inspection information includes an inspection ID, a patient ID, patient's name, the kind and condition of the inspection. Note that the present embodiment refers to a case where the CT inspection was carried out, so the thickness of slicing is included as one factor of the condition of the inspection. The memory 27 is a work memory that the CPU 26 uses for processing. The communication I/F 29 controls the data communication via the LAN 14 according to a communication protocol of the LAN 14.

The CPU 26 supervises the components of the medical report making terminal 13, and also executes the medical record making program to function as a report producer 26a, an image display controller 26b, an area designator 26c, an image choosing processor 26d, a grouping processor 26e and a linkage processor 26f.

Figure 3:
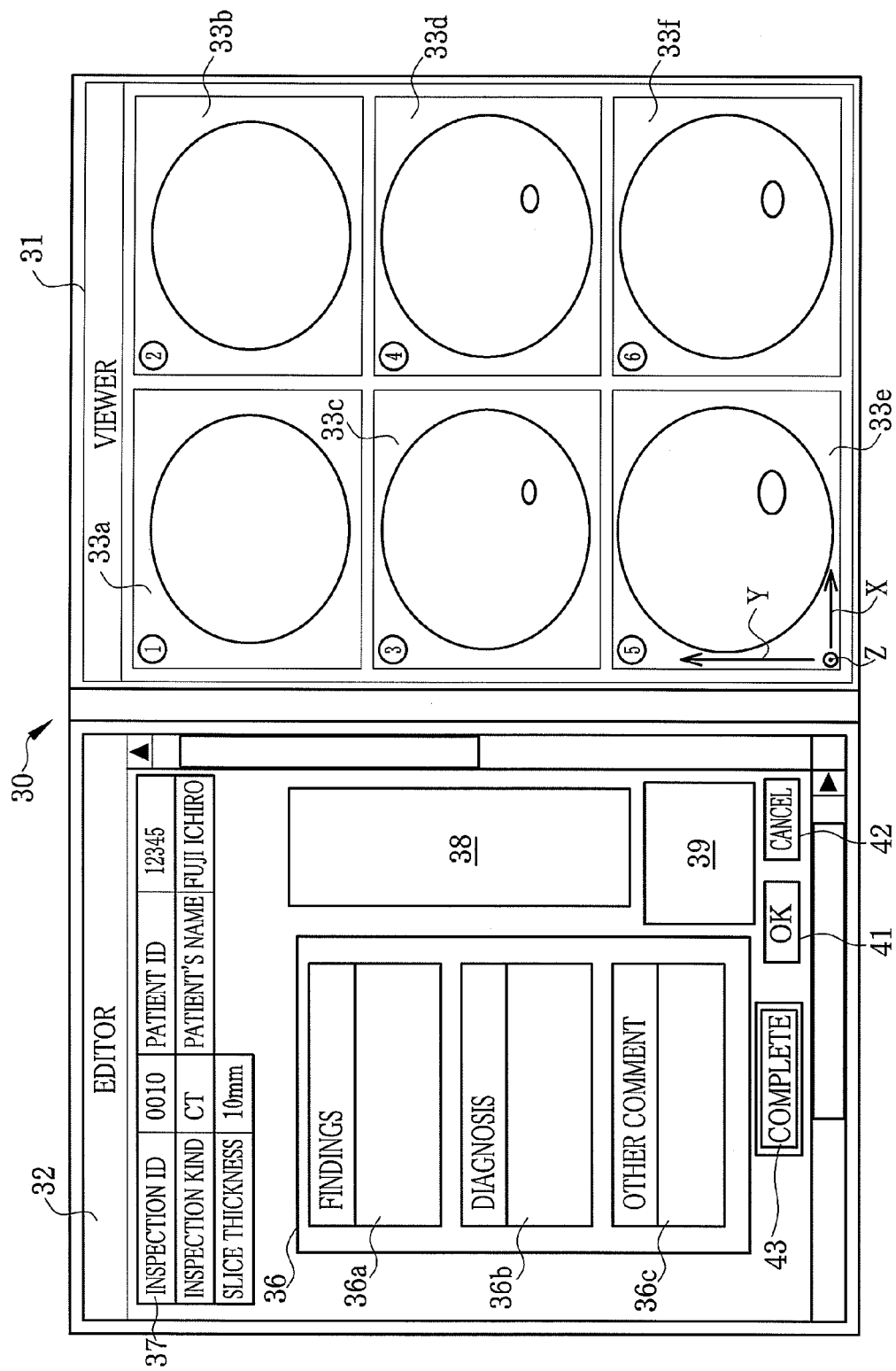
FIG. 3 is an explanatory diagram illustrating an example of a report making screen.

The image display controller 26b works for activating the monitor 21 to display a report making screen 30 as shown in FIG. 3. The report making screen 30 consists of a viewer 31 and an editor 32, which are apposed on the right and the left of the screen 30. The viewer 31 constitutes an image display device, whereas the editor 32 constitutes an editorial zone display device. The viewer 31 displays medical images as read out from the image database 16. Concerning such an inspection that takes a plurality of images at one time, like a CT inspection and an MRI inspection, the viewer 31 displays all of the medical images taken at one medical inspection. FIG. 3 shows an example, wherein six medical images (tomograms) 33a, 33b, 33c, 33d, 33e and 33f, which were taken by a CT inspection, are displayed in the viewer 31. These medical images 33a to 33f are a series of images taken successively from a patient, and represent surfaces taken by slicing the patient along perpendicular planes to a body axis of the patient at constant intervals of slicing. The medical image 33a is numbered with #1, indicating that this image was taken at the lowest position of the patient among the six medical images 33a to 33f. The following images 33b to 33f are numbered with #2 to #6 respectively, indicating the sequence from the lowest slicing plane. Not that a coordinate system is defined with respect to these medical images 33a to 33f, wherein X-axis and Y-axis directions of the coordinate system represent longitudinal and lateral directions of the slicing plane respectively, whereas a Z-axis direction represents the perpendicular direction to the slicing planes, i.e. the body axis direction.

The editor 32 displays a comment editing zone 36, an inspection information display zone 37, a chosen image display zone 38, a confirmation image display zone 39, an OK button 41, a cancel button 42 and a complete button 43. The inspection information display zone 37 is for displaying the inspection information obtained from the HDD 28.

The comment editing zone 36 is provided with comment columns 36a, 36b and 36c for writing a finding, a diagnosis and other remarks, respectively. A doctor in charge of the image-interpretation may input comments therein by operating the mouse 23 and the keyboard 24, the comments present a result of image-interpretation of the medical images 33a to 33f as displayed on the viewer 31. In the illustrated example, a lesion is found in the images 33c to 33f, so the comments on this lesion are written in the comment column 36a for the findings. When the comment is input in the comment editing zone 36, the linkage processor 26f operates to link information on the medical images to a designated position of the comments.

The chosen image display zone 38 is for displaying medical images that is chosen from among the medical images 33a to 33f displayed in the viewer 31, as will be described later.

The image display controller 26b also has a function to display such a confirmation image in the confirmation image display area 39 that is produced by processing a plurality of tomograms. According to the present embodiment, the image display controller 26b reconstitutes a three-dimensional image from the chosen medical images, using a well-known three-dimensional graphic display method, and displays the three-dimensional image as the confirmation image in the confirmation image display zone 39.

Figure 4:
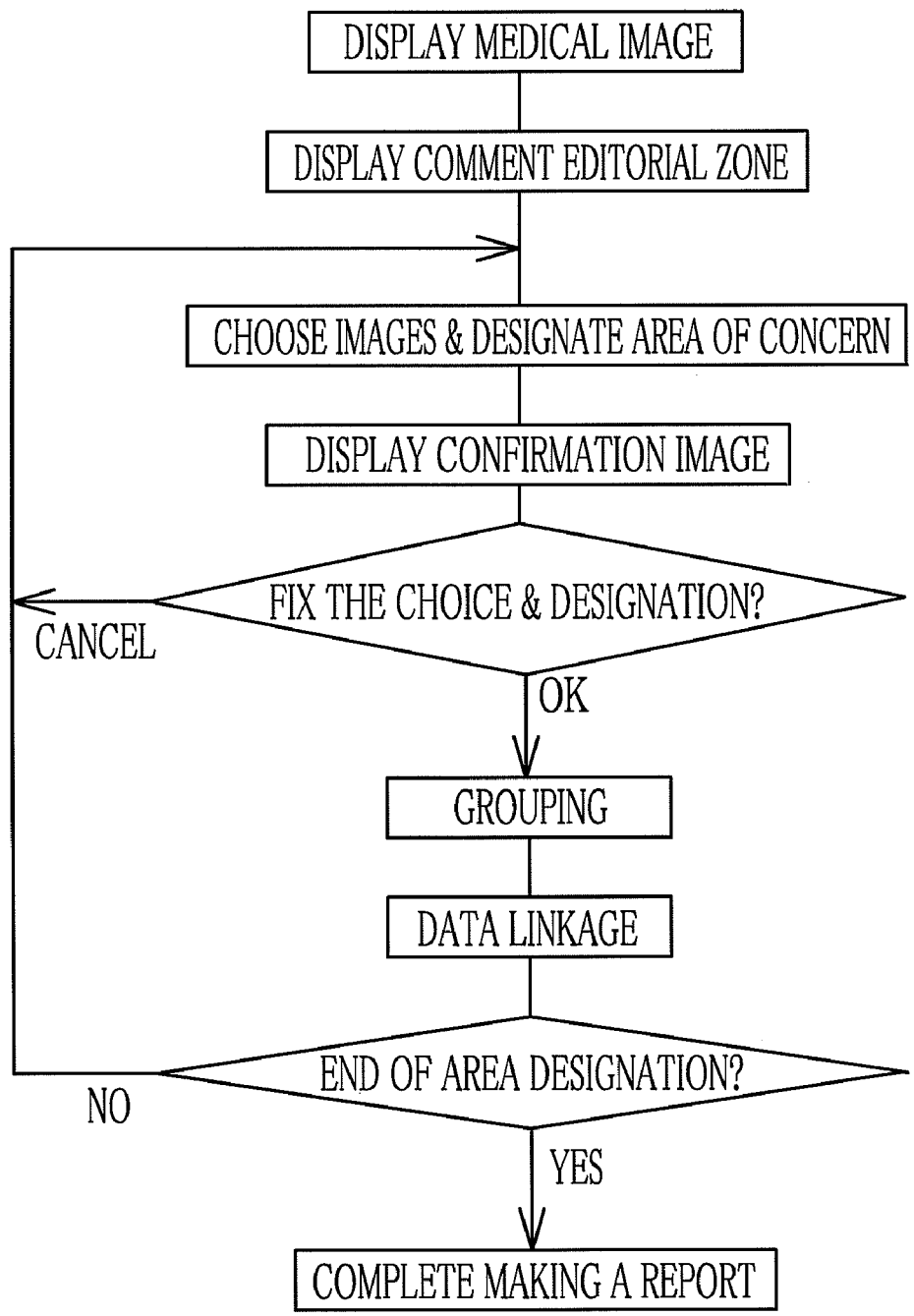
FIG. 4 is a flowchart illustrating a process of making a report.

Now procedures from inputting comments, choosing images to fixing the chosen images to complete a medical report making process will be described with reference to the flowchart show in FIG. 4.

When an interpreting doctor in the image-interpretation room 7 is making a medical report on the medical report making terminal 13, the doctor operates the console 19 to input an inspection ID. Then, the medical report making terminal 13 accesses the image server 11, to obtain from the image database 16 those medical images which are associated with the input inspection ID. Simultaneously, the medical report making terminal 13 reads out those inspection information which are associated with the input inspection ID from the HDD 28. Thereafter, the medical report making terminal 13 displays the report making screen 30 on the monitor 21, so the interpreting doctor makes the medical report according to the report making screen 30.

Concretely, the interpreting doctor inputs comments in the respective comment columns 36a to 36c, as a result of interpretation of the medical images 33a to 33f displayed in the viewer 31. Thereafter, the interpreting doctor makes an area designation process for designating an area of concern, which includes an affected site, in the individual medical image by operating the console 19. For example, the doctor clicks the mouse 23 while outlining the affected site in the image. Then, the area designator 26c is activated to designate the outlined affected site as an area of concern 45, as shown in FIG. 5A. To make it obvious that the area of concern 45 is designated, the area of concern 45 is displayed differently from other portion of the image. For example, the area of concern 45 has a different brightness, the outline of the area of concern 45 is definitely shown in the image, or the area of concern 45 is displayed in a conspicuous color like red or blue.

As a device for designating an area of concern in a medical image, it is possible to use a well-known CAD (computer aided diagnosis) system for extracting a contour of an abnormal shadow automatically from data of the medical image, and designate the range of the abnormal shadow as an area of concern. Although the area of concern 45 is designated along the outline of the affected site or the abnormal shadow, it is possible to designate a range around the affected site or the abnormal shadow as the area of concern 45.

When the area of concern 45 is designated in every image that shows the affected site, i.e. in the medical images 33c to 33f in the illustrated example, as shown in FIG. 5A, the image choosing processor 26d operates to choose these medical images 33a to 33f, and writes the chosen medical images 33c to 33f in the memory 27. Then, the chosen images 33c to 33f, the images #3 to #6, are fringed with a frame 46, to show that these images #3 to #6 are chosen, as shown in FIG. 5B.

Figure 6:
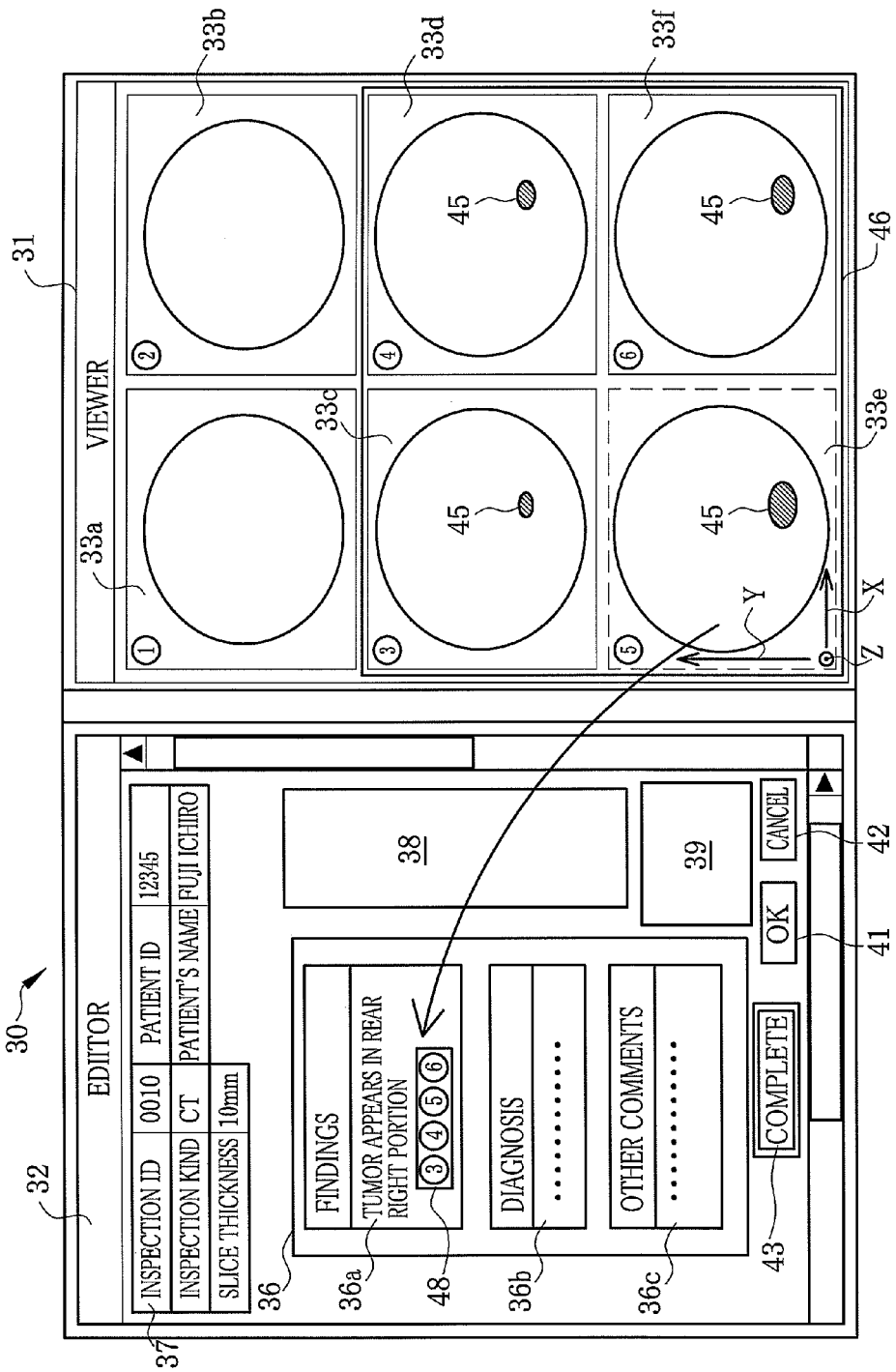
FIG. 6 is an explanatory diagram illustrating an operation for linking data to an assigned position of comments in a medical report.
Figure 7:
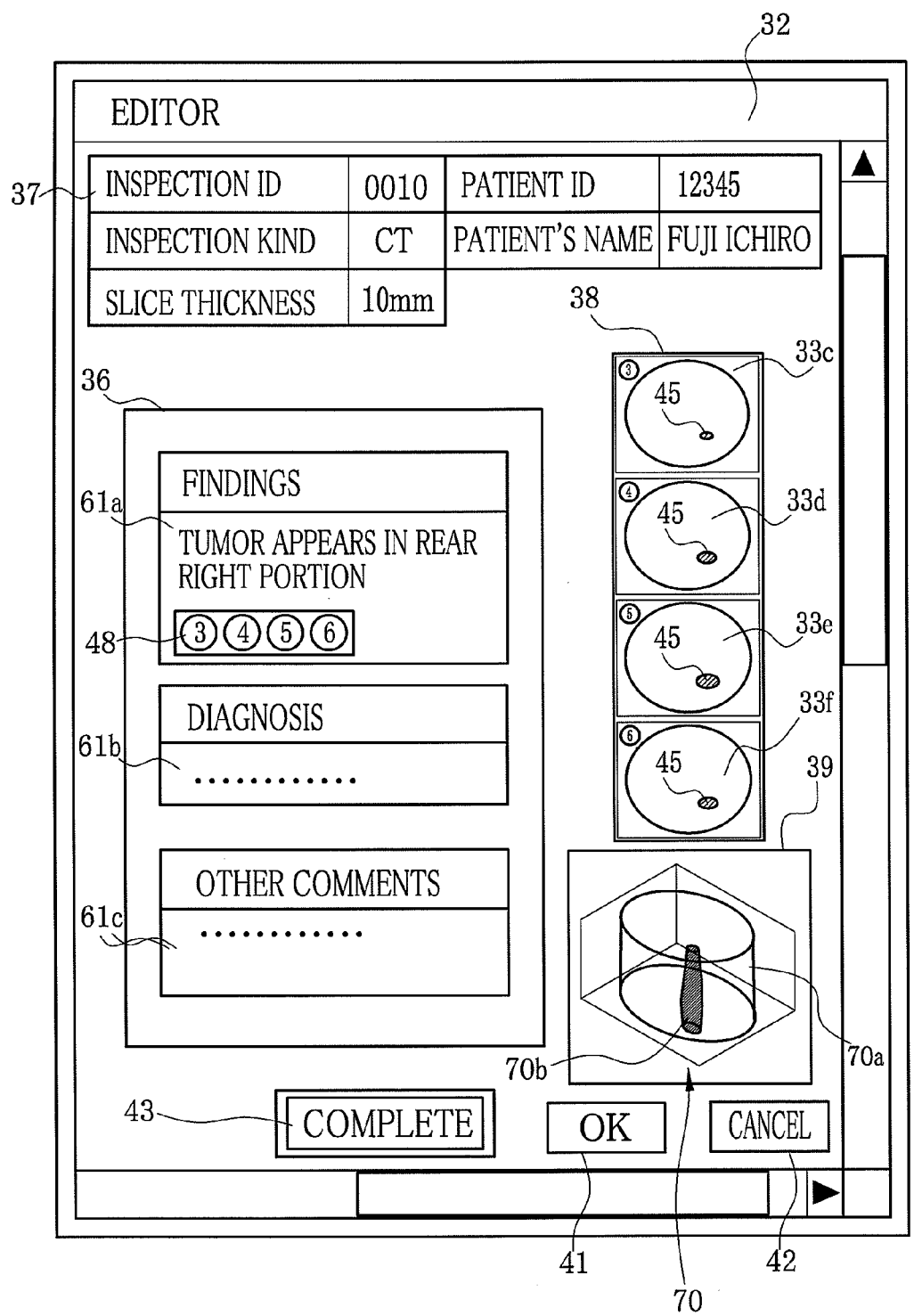
FIG. 7 is an explanatory diagram illustrating an example of the report making screen displaying an image for confirmation.

Thereafter, the interpreting doctor operates the mouse 23 to drag one of the chosen images 33c to 33f and drop it while placing the pointer of the mouse 23 near the comments input in the comment column 36a for findings, as shown for example in FIG. 6. Then, the image display controller 26b operates to display the chosen images 33c to 33f in the chosen image display zone 38, as shown in FIG. 7, and a three-dimensional image 70 reconstituted of the chosen images 33c to 33f is displayed as a confirmation image in the confirmation image display zone 39.

In order to display the three-dimensional image 70 reconstituted of the chosen images 33c to 33f, it is necessary to input the slice thickness "t" used for capturing these medical images 33c to 33f. Since the slice thickness "t" has been input as one of the inspection information in the present embodiment, the slice thickness "t" is read out from the HDD 28. But it is possible to input the slice thickness "t" through the console 19 of the medical report making terminal 13, or associate data of the slice thickness "t" with the medical images 33a to 3f in advance and read the data according to the need.

Figure 8:
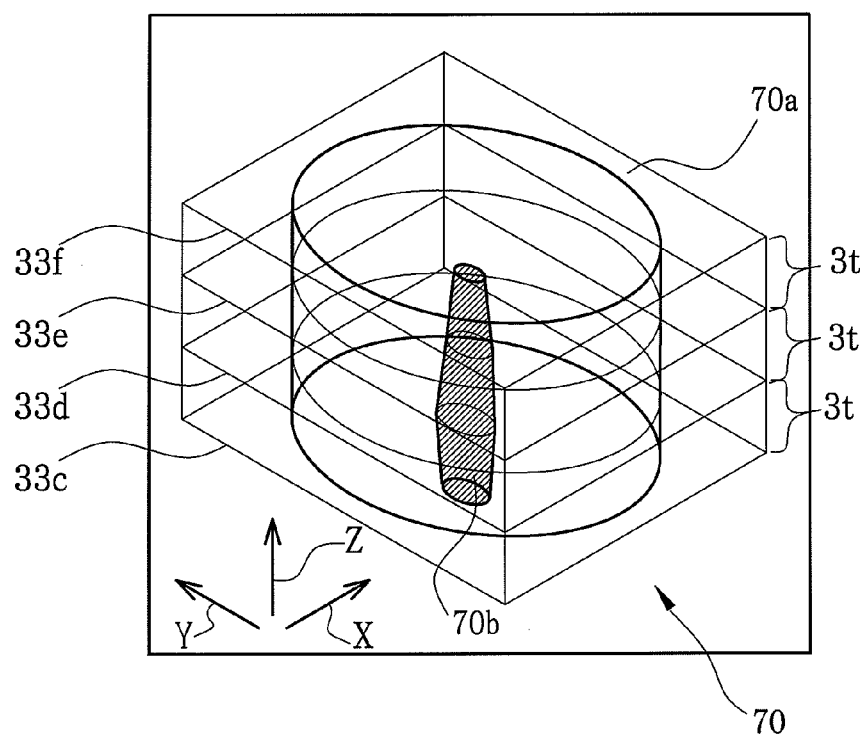
FIG. 8 is an explanatory diagram illustrating an example of a three-dimensional image in a case where medical images are correctly chosen and an area of concern is correctly designated.

The three-dimensional image 70 is reconstituted in a manner as shown in detail in FIG. 8, wherein the chosen medical images 33c to 33f are aligned so that their coordinative positions coincide with one another in the X- and Y-axis directions of the above-mentioned coordinate system, stacked up from the lower splicing plane to the upper slicing plane, and spaced apart from each other in the Z-axis direction at a constant interval defined based on the slice thickness "t". The interval between the images may be a multiple of the slice thickness. In the present embodiment, a triple "3 t" of the slice thickness "t" is used as the interval. Thereby, the imaged site and the area of concern are enhanced in size in the Z-axis direction, i.e. the body axis direction. Of course, it is possible to use the actual slice thickness "t" for the reconstitution process. As for the area of concern 45 that is contained in the medical images 33c to 33f, the same process as above is executed to reconstitute it as a three-dimensional image, and the three-dimensional image 70b of the area 45 is superimposed on a three-dimensional image 70a of the whole imaged site, to display them as the confirmation image 70 in the confirmation image display zone 39. At that time, using data on the position of the area of concern 45, which is associated with the medical report, the three-dimensional image 70b of the area of concern 45 is displayed in the three-dimensional image 70a of the whole imaged site to show the actual position of the area of concern 45 in the whole imaged site. Moreover, the three-dimensional image 70b of the area of concern 45 is displayed in a different manner, e.g. in a different color, from other portions of the image 70.

When the above-described image choosing process for choosing the medical images 33c to 33f and the area designation process for designating the area of concern 45 as well are worked out correctly, the three-dimensional image 70 is displayed in the confirmation image display zone 39, as shown in FIG. 8, wherein the three-dimensional images 70a and 70b are smooth continuous images.

Figure 9:
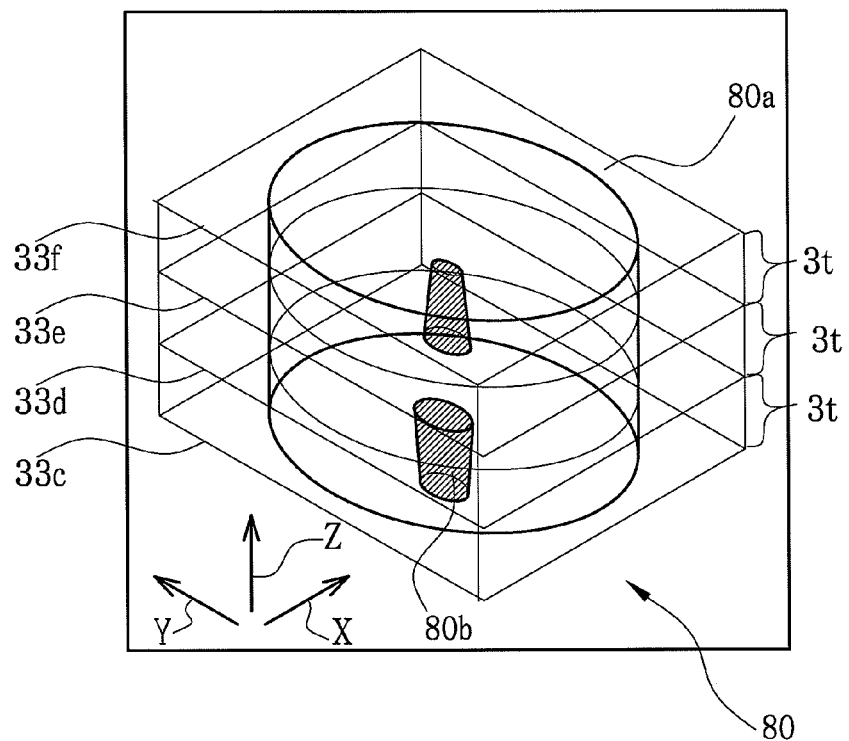
FIG. 9 is an explanatory diagram illustrating an example of a three-dimensional image in a case where some of medical images are wrongly chosen or an area of concern is wrongly designated.

If, on the contrary, a wrong medical image is chosen in the image choosing process, or a wrong area is designated in the area designation process, a three-dimensional image 80 like as shown in FIG. 9 will be displayed in the confirmation image display zone 39. In the illustrated example, the area of concern 45 is wrongly designated in the medical image 33d among the chosen ones 33c to 33f. Therefore, a three-dimensional image 80b of the area of concern 45 discontinues in the second lowest plane. Thus, the interpreting doctor instantly sees from the three-dimensional image 80 that the designation of the area of concern 45 is wrong in the medical image 33d, which corresponds to the second lowest plane among the chosen medical images 33c to 33f. If the choice of any medical image is wrong, the three-dimensional image 80a will not be continuous, so the interpreting doctor can visually recognize the error in choosing the image.

As described so far, displaying a three-dimensional image as a confirmation image makes it easy for the interpreting doctor to check if any medical image is wrongly chosen or if the area of concern is wrongly designated in any of the chosen images. When the confirmation image displayed in the confirmation image display zone 39 is the smooth continuous three-dimensional image 70, the interpreting doctor clicks on the OK button 41 to input data of fixing the chosen images and the designated areas. If, on the contrary, the discontinuous image 80 is displayed in the confirmation image display zone 39, the interpreting doctor clicks on the cancel button 42 to input cancel data as he or she recognizes the mistake in choice of the images or the area of concern. When the cancel data is input, the image choosing processor 26d cancels the choice of the medical images to be displayed in the viewer 31 as well as the designation of the area 45. Namely, the data of the chosen medical images 33c to 33f are erased from the memory 27, and the viewer 31 and the editor 32 are reset to the previous condition.

On the other hand, when the data of fixing the choice of the medical images 33c to 33f is input, the grouping processor 26c operates to produce group data indicating that the medical images 33c to 33f, the images #3 to #6, form a group, and the group data is written in the memory 27.

After the grouping process, the linkage processor 26f operates to link an assigned position 48 of the comments, which has been assigned by the above-described drag-and-drop operation of the mouse 23, with the group data as well as position data relating to respective locations (place and size) of the area of concern 45 in the medical images 33c to 33f of the group, and memorizes the linked data with the comments. At the completion of the data linkage process, the display of the assigned position 48 remains, whereas the viewer 31 is reset to display no image. If there is another area of concern such as a lesion beside the area of concern 45, the other area is designated or outlined in the same way as for the area of concern 45 by choosing corresponding images and confirming the chosen images. Also like the area of concern 45, numbers of the chosen medical images are displayed in a position assigned by the drag-and-dropping.

When the interpreting doctor completes inputting the comments, choosing the images, designating the area and confirming the chosen images, the doctor clicks on the complete button 43. Then, the report producer 26a operates to make a medical report that includes the comments and the data linked with the comments, and store the medical report in the report database 17.

As described above, the medical report produced on the medical report making terminal 13 may be read out from the report database 17, to display the comments and the images linked with the comments. Although the following description relates to a case where the medical report is retrieved on other terminal than the medical report making terminal 13, it is possible to retrieve and display the medical report on the medical report making terminal 13.

Figure 10:
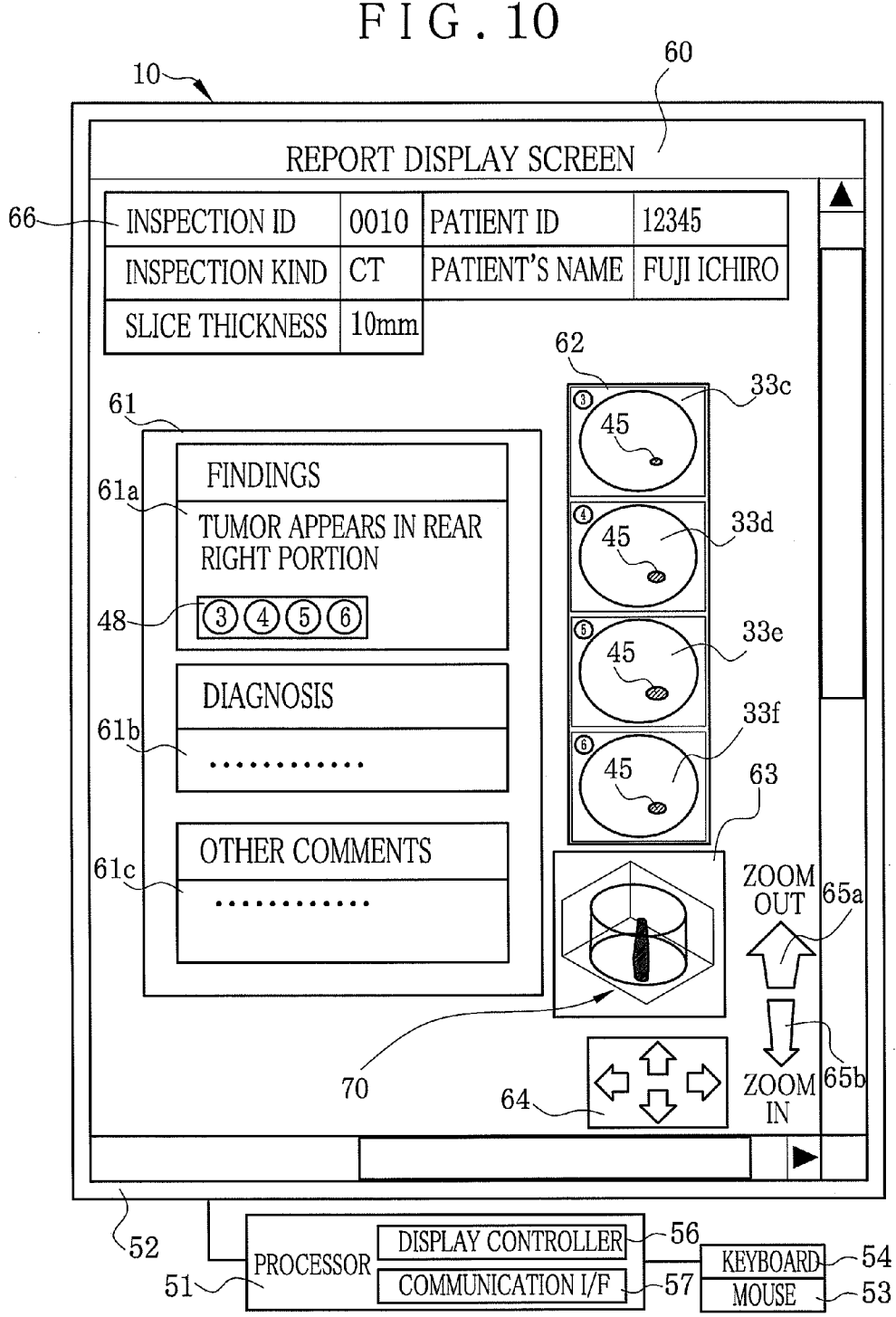
FIG. 10 is an explanatory diagram illustrating an example of a report display screen.

In the present embodiment, the medical report is retrieved and displayed on one of the diagnosis-and-treatment department terminals 10, so that a doctor who belongs to a diagnosis-and-treatment department and requested an examination may read the medical report on the requested examination. The diagnosis-and-treatment department terminal 10 is comprised of a processor 51, a monitor 52, a mouse 53 and a keyboard 54, as shown in FIG. 10. The processor 51 is provided with a display controller 56 and a communication I/F 57, and is installed with a browser, so that a report display screen 60, as shown in FIG. 10, is constituted and output on the monitor 52 as a medical report is obtained from the report database 17.

As an inspection ID is input to the diagnosis-and-treatment department terminal 10, the diagnosis-and-treatment department terminal 10 accesses to the report server 12 to obtain a medical report through the LAN 14. The diagnosis-and-treatment department terminal 10 receives the medical report, reads the group data linked with the comments in this medical report, and the position data relating to the area of concern of the medical images that belong to the group indicated by the group data, and obtains data of these medical images from the image database 16. After retrieving the medical report and the medical images, the diagnosis-and-treatment department terminal 10 displays the report display screen 60 on the monitor 52. The report display screen 60 is provided with a comment display zone 61 for displaying the comments as input on the report making screen 30, a linked image display zone 62 for displaying all medical images of one group that is linked to the assigned position 48 of the comment column, a confirmation image display zone 63, a cursor button 64, a couple of zoom buttons 65a and 65b and an inspection information display zone 66.

The comment display zone 61 displays the comments input by the interpreting doctor, and numbers #3 to #6 indicating the medical images 33c to 33f that are linked with the assigned position 48 of the comments. Upon clicking on these numbers #3 to #6, all the medical images 33c to 33f, which are linked with the assigned position 48 and registered as one group, are displayed in the linked image display zone 62. At the same time, the three-dimensional image 70, which is reconstituted of these images 33c to 33f, is displayed in the confirmation image display zone 63. Since the position data relating to the area of concern 45 in each of the medical images 33c to 33f is read in, the area of concern 45 is displayed in such a manner that it is visually distinguishable from other portions, e.g. in a different color from other portions. In a case where there are more than one assigned position in the comment display zone 61, the medical images displayed in the linked image display zone 62 as well as the three-dimensional image 70 displayed in the confirmation image display zone 63 are switched over according to which assigned position is clicked. As for the three-dimensional image 70 displayed in the confirmation image display zone 63, the display controller 56 of the department terminal 10 may be provided with a confirmation image display function for reconstituting the image 70 of the medical images 33c to 33f, or it is possible to store the three-dimensional image 70 as it is produced in the medical report making terminal 13 so that the department terminal 10 obtains the image 70 together with the medical report.

While the medical images 33c to 33f are displayed in the linked image display zone 62, they are scrollable in a direction indicated by an arrow of the cursor button 64 as the arrow is clicked on. Thereby, the area of concern 45 is movable to a center of each image. Upon clicking on the zoom button 65a or 65b, the respective images are zoomed in or out in the linked image display zone 62. It is possible to designate at least one medical image among those displayed in the linked image display zone 62, and zoom in or out or scroll the designated image alone.

As described so far, the interpreting doctor operates the medical report making terminal 13 to choose those medical images from among many ones, which contain at least an area of concern, and designate the area of concern in the chosen medical images. Then, the medical report making terminal 13 reconstitutes a three-dimensional image on the basis of the chosen medical images and the position data of the area of concern, and displays the three-dimensional image as a confirmation image. From the confirmation image, the interpreting doctor may instantly notice a mistake if there is any in the choice of the images or the designation of the area of concern. After confirming that the choice of the images and the designation of the area of concern are correct, the interpreting doctor completes the medical report and stores it. Therefore, the doctor who requested the medical report can observe the medical images, which were correctly chosen as containing the area of concern, simultaneously with the medical report. Thus, the accuracy of diagnosis based on the medical report will be improved.

Figure 11:
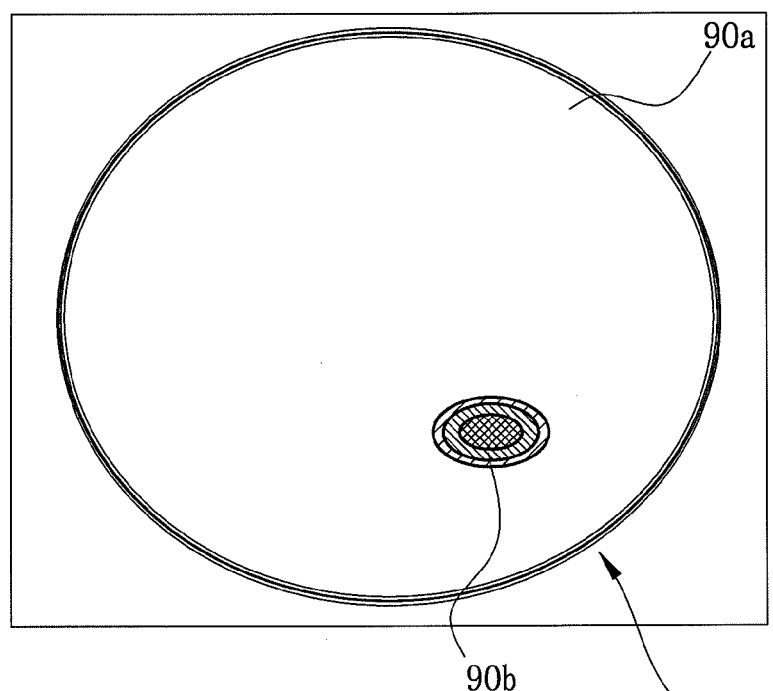
FIG. 11 is an explanatory diagram illustrating an example of a density-added image in a case where medical images are correctly chosen and an area of concern is correctly designated.
Figure 12:
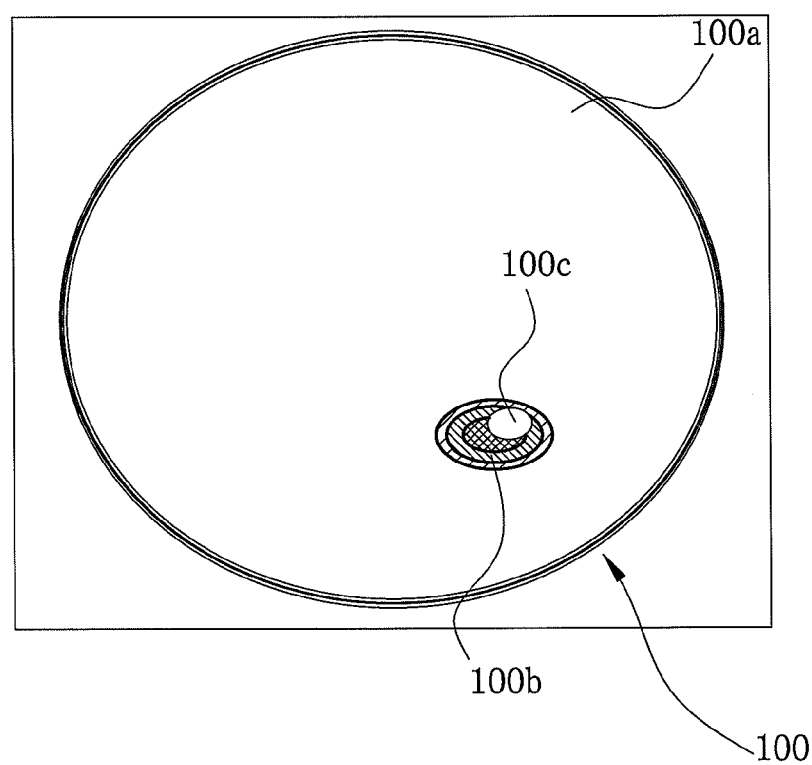
FIG. 12 is an explanatory diagram illustrating an example of a density-added image in a case where some of medical images are wrongly chosen or an area of concern is wrongly designated.

Although the above-described embodiment refers to the three-dimensional image as an example of the confirmation image obtained by processing the chosen medical images by use of the slice thickness for the tomography, the present invention is not limited to this embodiment. For example, a confirmation image may be a density-added image that is composed of the chosen images by adding density values at respective coordinate points, i.e. density values of respective pixels, of one image to density values at corresponding coordinate points of another image. FIGS. 11 and 12 show an embodiment, wherein the density-added image is formed as the confirmation image. Note that the medical images 33c to 33f are chosen in this embodiment like the above embodiment. If the medical images 33c to 33f are correctly chosen in the above-described choosing process, and an area of concern is correctly designated in the area designation process, a density-added image 90 is displayed as a confirmation image, as shown in FIG. 11, wherein both an image 90a of the whole area of the imaged site and an image 90b of the area of concern 45 are smooth continuous images. Since the density values of the chosen images are added at each coordinate point, a density distribution is displayed especially in the image 90b of the area of concern 45, so the confirmation image 90 reproduces a clear density graduation like a 2D contour map.

If, on the contrary, a wrong medical image is chosen in the image choosing process, or a wrong area is designated in the area designation process, a density-added image 100 like as shown in FIG. 12 will be displayed in the confirmation image display zone 39. In the illustrated example, the area of concern 45 is wrongly designated in the medical image 33d among the chosen ones 33c to 33f. Therefore, an image 100b of the area of concern 45 has a discontinuation 100c in the density gradation, where the density distribution remarkably differs from its periphery and looks unnatural. Thus, the interpreting doctor instantly sees from the image 100 that the designation of the area of concern 45 is wrong in any of the medical images 33c to 33f. If the choice of any medical image is wrong, a density-added image 100a of the whole imaged site will not be continuous, so the interpreting doctor can visually recognize the error in the choice of the images.

In the above embodiment, the confirmation image is produced by processing the chosen images and displayed on the medical report making apparatus (the report making terminal 13 in the inspection department 4) in order to check whether the images are correctly chosen or not as well as whether the area of concern is correctly designated or not. However, the present invention is not limited to this embodiment. For example, it is possible to notify the medical report making terminal 13 of a mistake in the choice of images or in the designation of an area of concern when the mistake is found in the confirmation image that is displayed in the medical report, to warn a need for choosing images or designating the area of concern again.

Although the report making screen and the report display screen display the comments written in the report and the medical images at the same time in the above embodiment, it is possible to provide a monitor for displaying medical images separately from a monitor for displaying information including comments written in a report.

In the above embodiment, an assigned position of the comment editing zone 36 is linked to group data and position data relating to the position of the area of concern in each of the medical images of that group. But it is possible to make linkages between various positions in the comment editing zone 36 respectively with different group data and position data relating to an area of concern in each medical image of the linked group.

Thus, the present invention is not to be limited to the above embodiments but, on the contrary, various modifications will be possible without departing from the scope of claims appended hereto.

What is claimed is:

1. A medical report system for making and displaying a medical report, comprising:
   an image display device for displaying a number of medical images taken from a test body;
   an image choosing device for choosing some medical images from among the displayed medical images; and
   an image display control device for processing data of said chosen medical images to produce and display a confirmation image on said image display device or another image display device, wherein said confirmation image represents an imaged site of said test body contained in said chosen images and is configured in a three-dimensional coordinate system with respect to a body axis of said test body.

2. A medical report system as recited in claim 1, further comprising:
   an area designating device for designating an area of concern in said medical images, wherein said image choosing device chooses those medical images which contain the area of concern as designated by said area designating device, and said image display control device distinguishes the designated area and displays the designated area in a different manner from other portion in said confirmation image.

3. A medical report system as recited in claim 1, wherein said medical images are tomograms taken from said test body along parallel slicing planes, and said image display control device reconstitutes from said chosen images a three-dimensional image of said imaged site as said confirmation image, wherein said chosen images are stacked up sequentially from the lower plane to the upper plane and are spaced from one another in an Z-axis direction of said coordinate system that is perpendicular to said slicing planes, at a constant interval defined based on a slice thickness used for tomography, and respective pixels of one chosen image are aligned with those pixels of another chosen image which correspond in XY coordinative position in said coordinate system.

4. A medical report system as recited in claim 1, wherein said medical images are tomograms taken from said test body along parallel slicing planes, and said image display control device produces a density-added image from said chosen images by adding density values of respective pixels of one chosen image to density values of those pixels of another chosen image which correspond in position in XY directions of said coordinate system, which are parallel to said slicing planes, and displays said density-added image as said confirmation image.

5. A medical report system as recited in claim 2, further comprising:
   a device for displaying and editing a report making screen that has a comment editing zone for inputting and editing comments on said medical images;
   a grouping device for producing group data that registers said chosen images as one group each time the choice of these medical images is fixed; and
   a linking device for storing said group data and position data relating to respective positions of said area of concern in said chosen images while making a linkage of said group data and said position data to an assigned position in said input comments.

6. A medical report system as recited in claim 5, further comprising a device for displaying a medical report as made on said report making screen, wherein said image display control device displays said chosen images and said confirmation image on said medical report based on the group data and the position data stored relating to the assigned position when said assigned position in said input comments is selected on said medical report.

7. A medical report system as recited in claim 2, further comprising a device for extracting an abnormal shadow automatically from data of said medical images, wherein said area designating device designates said extracted abnormal shadow as said area of concern.

8. A medical report making apparatus for making a medical report, comprising:
   an image display device for displaying a number of medical images taken from a test body;
   a device for displaying and editing a report making screen that has a comment editing zone for inputting and editing comments on said medical images;
   an image choosing device for choosing some medical images from among the displayed medical images; and
   an image display control device for processing data of said chosen medical images to produce and display a confirmation image on said image display device or another image display device, wherein said confirmation image represents an imaged site of said test body contained in said chosen images and is configured in a coordinate system with respect to a body axis of said test body.

9. A medical report making apparatus as recited in claim 8, further comprising:
   an area designating device for designating an area of concern in said medical images, wherein said image choosing device chooses those medical images which contain the area of concern as designated by said area designating device, and said image display control device distinguishes the designated area and displays the designated area in a different manner from other portion in said confirmation image.

10. A medical report making apparatus as recited in claim 8, wherein said medical images are tomograms taken from said test body along parallel slicing planes, and said image display control device reconstitutes from said chosen images a three-dimensional image of said imaged site as said confirmation image, wherein said chosen images are stacked up sequentially from the lower plane to the upper plane and are spaced from one another in an Z-axis direction of said coordinate system that is perpendicular to said slicing planes, at a constant interval defined based on a slice thickness used for tomography, and respective pixels of one chosen image are aligned with those pixels of another chosen image which correspond in XY coordinative position in said coordinate system.

11. A medical report making apparatus as recited in claim 8, wherein said medical images are tomograms taken from said test body along parallel slicing planes, and said image display control device produces a density-added image from said chosen images by adding density values of respective pixels of one chosen image to density values of those pixels of another chosen image which correspond in position in XY directions of said coordinate system, which are parallel to said slicing planes, and displays said density-added image as said confirmation image.

12. A medical report making apparatus as recited in claim 9, further comprising a device for extracting an abnormal shadow automatically from data of said medical images, wherein said area designating device designates said extracted abnormal shadow as said area of concern.

13. A medical report making method comprising steps of:
- displaying a number of medical images taken from a test body;
- inputting and editing comments on said medical images in a predetermined zone on a displayed screen;
- choosing some medical images from among the displayed medical images;
- processing data of said chosen medical images to produce a confirmation image, said confirmation image representing an imaged site of said test body contained in said chosen images in a coordinate system defined with respect to a body axis of said test body; and
- displaying said confirmation image.

14. A medical report making method as recited in claim 13, further comprising steps of:
- producing group data that registers said chosen images as one group each time the choice of these medical images is fixed;
- producing position data relating to respective positions of said area of concern in said chosen images;
- assigning a position in said input comments; and
- storing said group data and said position data while making a linkage to said assigned position in said input comments.

* * * * *